United States Patent [19]

Au

[11] Patent Number: 4,813,436
[45] Date of Patent: Mar. 21, 1989

[54] MOTION ANALYSIS SYSTEM EMPLOYING VARIOUS OPERATING MODES

[75] Inventor: Jan C. Au, Lake Grove, N.Y.

[73] Assignee: Human Performance Technologies, Inc., Stonybrook, N.Y.

[21] Appl. No.: 79,582

[22] Filed: Jul. 30, 1987

[51] Int. Cl.$^4$ .............................................. A61B 5/10
[52] U.S. Cl. ................................. 128/779; 128/782
[58] Field of Search ................... 128/774, 779, 782; 358/105; 364/413, 415

[56] References Cited

U.S. PATENT DOCUMENTS

| | | | |
|---|---|---|---|
| 3,894,437 | 7/1975 | Hagy et al. | 128/779 |
| 4,267,728 | 5/1981 | Manley et al. | 128/779 |
| 4,323,973 | 4/1982 | Greenfield | 364/415 |
| 4,375,674 | 3/1983 | Thornton | 128/782 |
| 4,416,293 | 11/1983 | Anderson et al. | 128/779 |
| 4,554,930 | 11/1985 | Kress | 128/774 |
| 4,598,717 | 7/1986 | Pedotti | 128/779 |
| 4,600,018 | 7/1986 | Boyd et al. | 128/779 |
| 4,631,676 | 12/1986 | Pugh | 128/782 |
| 4,647,918 | 3/1987 | Goforth | 128/779 |

*Primary Examiner*—Max Hindenburg
*Attorney, Agent, or Firm*—Arthur L. Plevy

[57] ABSTRACT

A motion analysis system and apparatus incorporates markers which are secured at various joints of the subject's body as well as pressure sensitive shoes or insoles which are worn by the subject. The subject is caused to perform motion such as walking or running. While performing this motion, the subject is televised by means of two video cameras. The video signal from the cameras is stored by means of video recorders and then processed on a frame-to-frame basis to provide digitized data. The pressure sensitive insoles provide signals which are processed according to analog to digital conversion techniques whereby a display is also provided which indicates the pressure applied to the subject's foot while performing. The remaining data as supplied by the first and second video cameras and which is digitized is then further processed to present various displays showing the gait, the angular position of the various joints of the patient and various other information indicative of the particular walking characteristics of the subject. The data thus produced and processed by the system enables a practitioner to judge the persons's walking gait as compared to a normal user.

19 Claims, 10 Drawing Sheets

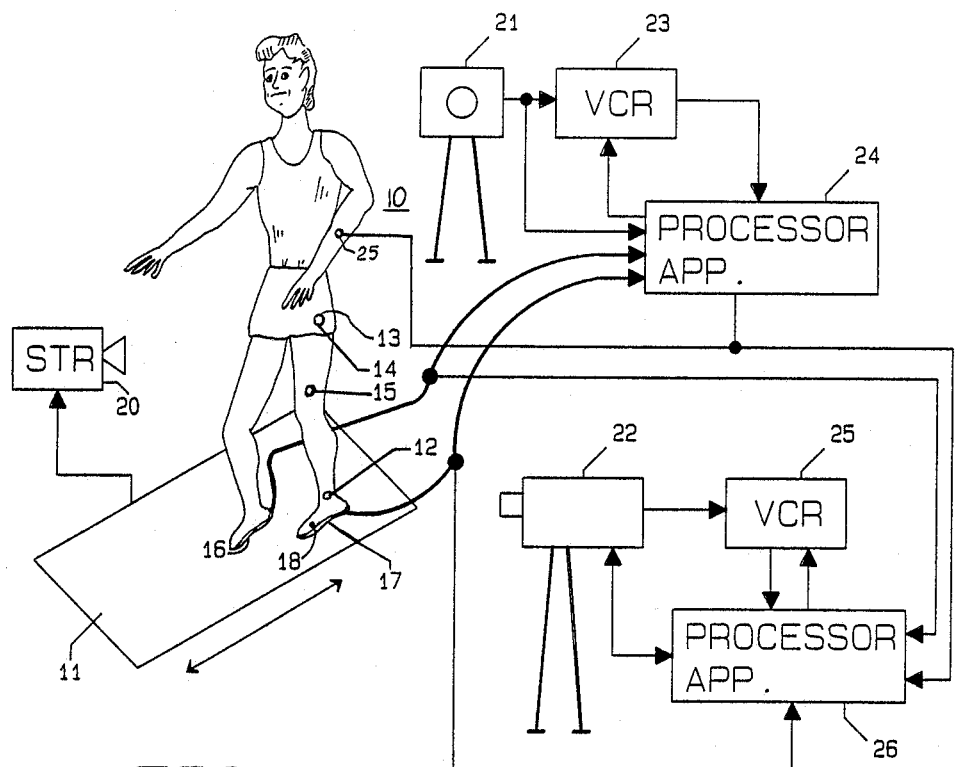
FIG. 1
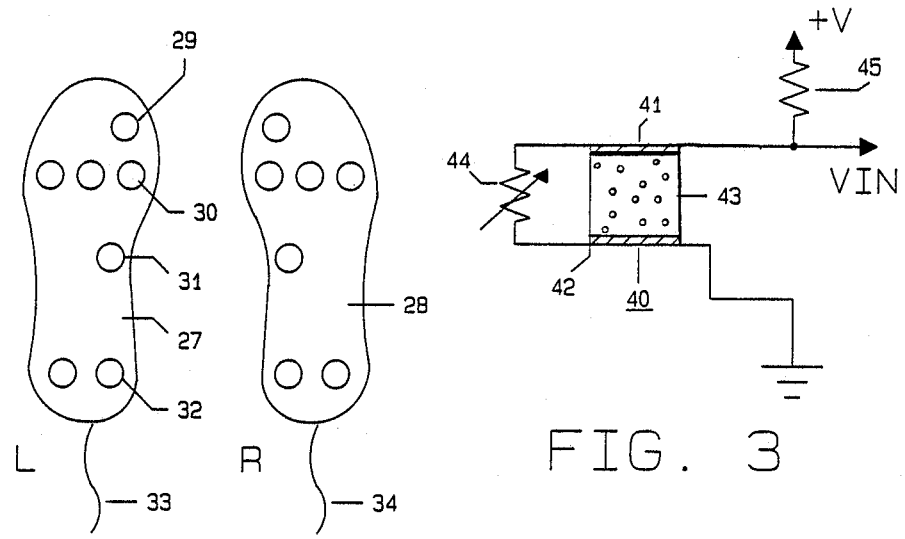
FIG. 2
FIG. 3

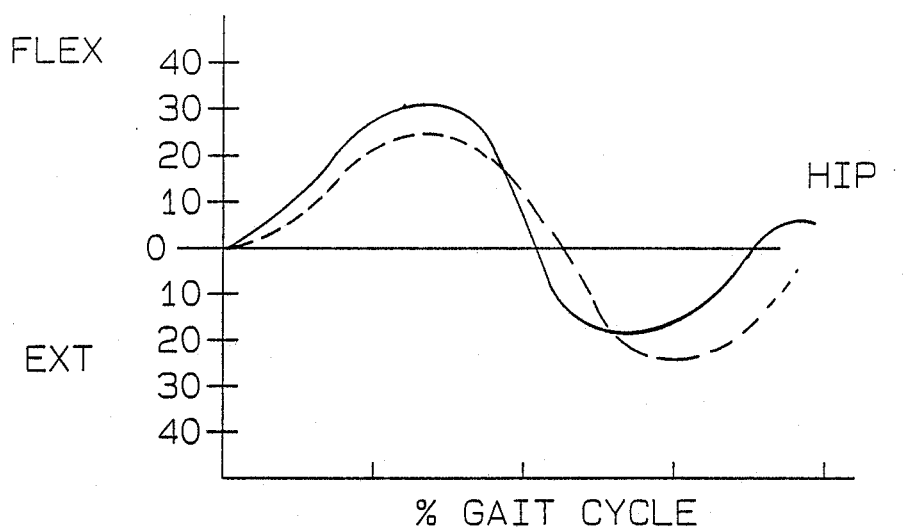
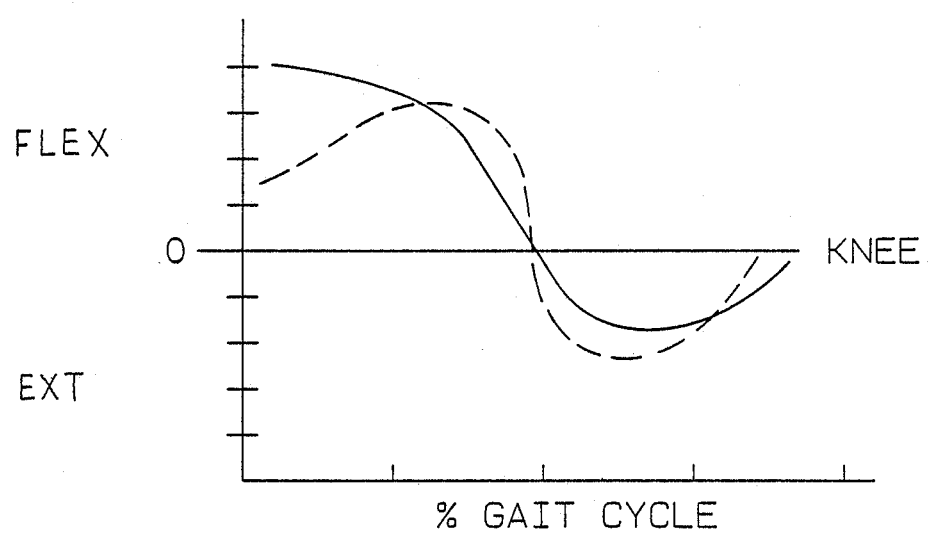
FIG. 9

MOTION ANALYSIS SYSTEM EMPLOYING VARIOUS OPERATING MODES

BACKGROUND OF THE INVENTION

This invention relates to a motion analysis system in general and more particularly to a real time motion analysis system for monitoring motion regarding gait and monitoring responses of a patient's foot and legs.

The art of motion analysis has been investigated and there exists many prior art systems which serve and operate to analyze motion. Such which are based on computer programs operating in conjunction with complicated algorithms. The compute decodes and deciphers data according to such algorithms in order to determine the motion patterns of an individual.

According to the operation of such systems various body processes such as the motion and angles between body joints can be analyzed while a patient or a person is performing a typical task. This task may relate to a person's gait while walking and such systems may further monitor the movement of joints such as the knee, toe and so on.

Human motion analysis allows one to determine limits and constraints on various body joints and use such determinations to assist the patient in performing physical activities more efficiently. As one can ascertain from the prior art, most systems employ video cameras and a tape recorder to record the events and retain suitable pictures which are analyzed by the practitioner to determine the extent of motion.

This data can be placed in a computer which based on the programs can reconstruct the motion in terms of various configurations such as stick figure configurations or other configurations which are widely employed and known. As indicated, the prior art is replete with various system which analyze human motion and which systems employ video television cameras and video recorders to process data emanating from such devices in order to generate meaningful computer displays.

See for example, an article entitled "An Automated Motion Measurement System For Clinical Gait Analysis" by Kenneth D. Taylor et al, published in *Biomechanics,* Vol. 15, No. 7, pp 505–516, 1982. This article describes an automated motion measuring system which employs a television camera interfaced to a computer. The system was constructed to evaluate clinical gait analysis. The system employs passive markers which are placed on a human torso which torso is illuminated with infrared light emitting diodes.

This approach according to the article minimizes patient distraction since the illumination is not visible and reduces patient discomfort. In any event, the motion measurement system has been employed and purportedly operates to perform the required task. The abovenoted article has a relatively extensive bibliography which references various other prior art systems which employ television cameras and tape recorders to record motion data. Essentially, the use of computers in general for tracking body motions is well known in the prior art and there are many other examples of such devices.

See for example an article entitled "Computer Aided Tracking Of Body Motion Using A C.C.D.-Image Sensor" by W. Brugger et al, published in *Medical And Biological Engineering and Computers,* Vol. 16, pp 207–210, March 1978. In that particular article there is described an image sensor which is employed to obtain on-line trajectories of moving objects in one plane. The image data acquired is stored and processed by several programs to yield displays which enable interpretation and measurements to be effected.

One aspect of the particular application of the system is in regard to kinesiological data allied with human locomotive functions. The prior art includes many patents related to motion analysis such as U.S. Pat. No. 4,375,674 issued on Mar. 1, 1983 to W. E. Thornton and entitled KINESIMETRIC METHOD AND APPARATUS. This patent discloses apparatus and methods for determination of functional capability of bodies. Certain aspects such as reach as well as velocity, acceleration and force generation at various positions are determined for a body by a three-dimensional kinesimeter equipped with an ergometer.

Thus, the patent shows techniques for measuring various trajectories provided by human movement which techniques employ television cameras to gather and process data.

Pursuant to such prior art approaches, reference is also made to U.S. Pat. No. 4,631,676 which issued on Dec. 23, 1986 to James W. Pugh and entitled COMPUTERIZED VIDEO GAIT AND MOTION ANALYSIS SYSTEM AND METHODS. In that patent there is described a system which employs reflective markers attached to the front side of particular joints of a subject whose motion or gait is to be analyzed. Each marker as indicated is formed of a reflective tape and is small so as not to hinder the subjects motion. The patent discloses and uses a pair of commercial video motion analyzers which operate at 60 frames per second and are positioned to the front and side of a walk path or runway.

The monitors coact with video cassette tape recorders which record the patient's movements along the runway. There are monitors which are provided for playback of the recorded video tape and include built-in magnetic disks allowing 10 seconds of a nigh speed motion to be recorded and displayed. The structure includes a video analysis board which essentially is a minicomputer and operates to digitize each recorded video frame to locate centroids of each of the reflective markers. This data is fed into a computer which operates on the data to provide line and stick figure displays of the data and which operate to depict the motions under study. Various other diagrams such as cyclograms of hip angle-knee angle relations for a cycle of movement are provided. As one can ascertain from this reference, there are various figures which show desirable outputs which are utilized by practitioners to study the gait of a particular patient as well as to provide other displays which are useful in analyzing motion.

In any event, as one can ascertain from the prior art, such systems which are operative to provide motion analysis are largely dependent upon processing techniques as well as requiring extensive software and computer time in order to solve such problems. There are substantial problems involved in acquiring analyzed data in conjunction with video tape recorders as well as employing computer processing techniques. Certain of these, as indicated above, can be circumvented by the use of algorithms.

In any event, various algorithms for such motion analysis are well known in the prior art. Such algorithms are intended for resolution of problems that include various discrepancies in video signals such as missing data points, statistical techniques to improve accuracy, searching routines and calibration programs. Such algorithms as indicated have been widely employed in the prior art to enhance the use of such systems.

In spite of the strides made in motion analysis according to such prior art techniques, there are many problems which still have to be solved. Such problems mainly relate to the complexity of the prior art systems and the extreme difficulty in reducing the cost and time involved in compiling and analyzing the data. As indicated, while most systems generally employ a video camera in conjunction with tape recorders and computers the adaptability is a pure function of the manner in which the data is analyzed as well as the various problems associated with tape recorders and video monitors. These operate in conjunction with computers in an attempt to establish proper and reliable operating levels in order to provide valid data indicative of the motion to be analyzed.

It is therefore an object of the present invention to provide a motion analysis system which is relatively inexpensive and which enables an accurate presentation of motion in real time.

It is a further object to provide a system which operates to eliminate many of the problems associated with the prior art.

Thus, the system to be described employs various unique techniques in order to assure reliability such as techniques for providing accurate synchronization between the various components, techniques for analyzing the proper location of various marking devices in order to provide proper graphic presentation of data and as well as other techniques.

As will be explained, the present invention also is capable of operating in various modes whereby in a first mode one can obtain pressure information concerning forces applied to the foot of a patient in regard to the toe heel and arch area when the patient is walking. Another mode of operation which can also be utilized in conjunction with the above mode enables one to provide accurate presentations in terms of stick figures of the gait of such a patient. This data therefore enables the practitioner to get an accurate and reliable view of a patient's gait in order to help the patient solve the problems that he may have.

BRIEF DESCRIPTION OF THE PREFERRED EMBODIMENT

A motion analysis system of the type operative to analyze the movements of designated body portions of a subject to be monitored as the subject walks along a predetermined path and to particularly analyze the pressure applied to the feet of said subject when traversing said path, comprising pressure responsive means secured to the feet of said subject and operative to provide output pressure signals indicative of the force applied to the subject's feet while traversing said path, first computer means coupled to said pressure responsive means and operative to analyze said pressure signals to provide a display of the pressure applied to said subject's feet during given selected time intervals as said subject traverses said path

BRIEF DESCRIPTION OF THE FIGURES

FIG. 1 is a schematic plan view depiction of a test subject performing a walking exercise before the motion analysis system according to this invention..

FIG. 2 is a bottom plan view of pressure sensitive test insoles which are worn by the subject of FIG. 1 when performing a walking exercise according to this invention.

FIG. 3 is a schematic representation of a typical pressure sensor which is used in the insoles of FIG. 2.

FIG. 9 are diagrams of other types of displays generated by the apparatus of this invention.

DETAILED DESCRIPTION OF THE FIGURES

Figure 4:
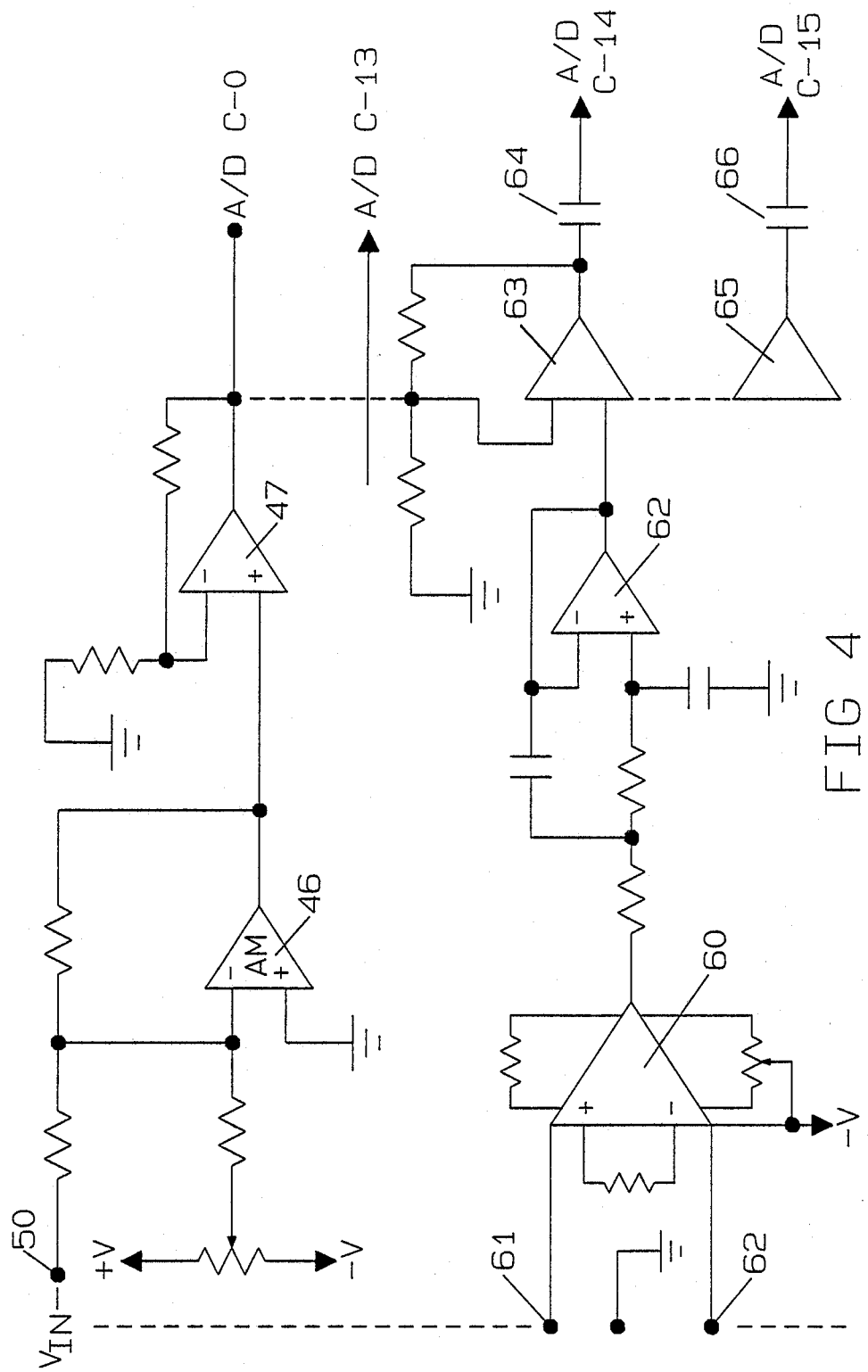
FIG. 4 is a schematic diagram of a plurality of amplifiers associated with the various sensors mounted or positioned on the subject of FIG. 1.

Referring to FIG. 1, there is shown a simple block diagram of a motion analysis system according to this invention.

As one can ascertain from FIG. 1, there is shown a pictorial representation of patient 10 who is walking along a path including a pressure sensitive mat 11. Essentially, referring to FIG. 1, the patient 10 has positioned on his hip, knee, ankle and toe various reflecting or marker devices designated as 13, 14, 15 and 18 respectively. These marker devices may be strips of reflective tape or may be LED devices which are capable of emitting infrared or other energy and can be visually observed or responded to by a suitable television camera. Such reflective devices as well as LED devices utilized as markers are well known and many examples of the same exist in the prior art.

It is also noted that certain of the prior art systems as described above utilize such reflective or direct illuminating markers. The markers 13, 14, 15, and 18 for example will be employed to provide gait analysis which is one aspect of this invention. The subject is also fitted with two pairs of pressure sensitive sandals or insoles which he wears as he is walking along the particular path.

The pressure sensitive sandals or insoles are designated respectively by numerals 16 and 17, and as will be explained, they may be coupled by means of cables to a processor apparatus 24 as well as to a processor apparatus 26. The processor apparatus as will be explained operates to process the data and to provide suitable signals for control of various monitors and displays associated therewith.

As one can ascertain from FIG. 1, there is a first and a second television camera designated respectively as 21 and 22. Each camera may for example be a C.C.D. device such as devices supplied by Sanyo of Tokyo, Japan. These devices are well known in the art and many television cameras exist which will be suitable for the operation of this system.

As seen in FIG. 1, the television camera 21 which provides a video signal is coupled to a video tape recorder or VCR 23. The VCR 23 associated With the television camera 21 is also coupled to a processor apparatus 24. As will be explained, the processor apparatus includes a microcomputer and various displays and monitors, all of which are operative to provide gait and other analysis of data which is provided this invention. Similarly, the television camera 22 is associated with a video tape recorder VCR 5 which is coupled to processor apparatus 26.

Apart from the reflective sensors which are located at the hip, knee, ankle and toe locations of the subject 10, there are other sensors such as sensor 25. These sensors are devices which monitor the respiration rate the amount of sweat, the muscle contractions of the individual and can be placed by the practitioner or physician who is utilizing the systems at optimum body locations. It is noted that the sensor 25 is merely indicative of one type of sensor which is a EMG sensor and which sensors are well known in the art and can be provided to monitor various muscle functions of the patient.

It is seen that the output from sensor 25 is also coupled to the processor apparatus 24 and 26 for motion analysis. Associated with the pressure sensitive mat 11, as will be explained, is a strobe light 20. The strobe as will be further explained is activated when the patient first makes contact with the pressure mat 11. In this manner a bright flash of light is generated by the strobe and responded to by the cameras 21 and 22. This, as will be explained, indicates that start of the processing of data and enables the practitioner by viewing the television picture to know exactly when contact was made by the patient with the pressure sensitive mat 11. Thereafter, all frames of video information are referenced to this strobed frame which essentially determines the start of the analysis.

To give one a brief insight to the operation of the invention, it is believed that a description of the system operation in conjunction with the simple diagram of FIG. 1 is warranted at this juncture. As will be seen, the apparatus of FIG. 1 includes a camera 21 and cameras 22 which as indicated are C.C.D. devices and are available from many sources.

The camera 21 monitors and provides the back and the front view of the subject 10 while the camera 22 provides a side view. The video output from cameras 21 and 22 are recorded on associated video recorders as 23 and 5 which are for example a Sony recorders designated and sold by Sony Manufacturing Company of Japan under the symbols HFSL 900. As indicated above, when the subject 10 first contacts the mat 11 which is a pressure sensitive mat, a signal is generated which causes the strobe 20 to be activated.

The strobe 20 generates a burst of white light and as triggered by the pressure sensitive mat. The burst is recorded for synchronization by means of both cameras 21 and 22. Each tape recorder output may be analyzed separately at 30 frames per second. Essentially, the starting point for analysis is the frame which occurs right after the f frame containing the strobe light. As one can ascertain, the strobe light duration is less than a frame and is approximately for example one half the frame rate. Thus, the strobe frame in the video analysis is characterized by excessive light indicative of the triggering of the strobe.

Hence, the frame right after the strobe frame is frozen by the system via a frame freeze technique and processed by the processing apparatus 24 and 26. The video signal thus generated by that frame is passed through an image enhancing circuit contained in the processor apparatus and is then digitized according to a particular format. The digitizing of a video signal to convert the same into a digital signal is a well known technique as will be explained.

As will be explained, each of the markers as for example 13, 14, 15 and so on are characterized by being brighter than other portions of the picture. In this invention, the marker locations are in fact determined by the practitioner by the use of a light pen which light pen is used to locate the marker position by allowing the practitioner to view the contents of the video tape.

The system also employs an edge detection algorithm program to determine the outline of the markers which outline or circumference is traced and the center of the marker or centroid is then calculated. In any event, in this system, if a marker is missing due to the particular walk of the use or the interference by other body parts then the operator will use the light pen or cursor to locate the proper joint position manually, and hence this system enables the insertion by means of a light pen or a cursor of missing markers.

As one can understand, during a walking procedure, the subject may turn away from a camera or may move his arm or hand so that an existing marker would be blocked. In any event, the practitioner knows that four markers are required and hence the practitioner can approximately determine the location of a marker by the use of a light pen and by viewing the display.

In this manner, after all the markers are located either by the automatic edge detection scheme or by the manual operation provided for above, the frame is advanced to the next frame and the above procedures are implemented in that each successive frame is frozen and enhanced and then digitized and stored. The markers associated with each subsequent frame are then located either by edge detection or by the manual means as described above.

At the end of the procedure, one will therefore have analyzed 30 frames per second and will positively be assured that each frame is properly identified in regard to marker position. It is, of course, understood that the above-described techniques can operate in conjunction with the pressure sensitive insoles as will be described subsequently. These insoles are capable of providing a completely separate display and different types of information to enable the practitioner to determine the pressure applied during a walking sequence on the feet of a user. The data will determine for example the heel pressure as compared to the arch or toe pressure or the pressure between the toe and arch and so on.

Referring to FIG. 2, there is shown front plan views of typical foot insoles or sandals which are associated with positioned pressure transducers. As seen from FIG. 2, there is a left and a right shoe as designated by numerals 27 and 28. Each of the shoes or sandals or foot insoles contain pressure transducer devices at various locations. As can be ascertained from FIG. 2, there are seven transducers associated with each insole as seven transducers for insole 27 indicative of the left foot and seven transducers for insole 28 indicative of the right foot.

As one can see, a first transduced 29 is located in the area of the big toe. There are then three transducers 30 located between the arch and the big toe. There is a transducer 31 at the arch area and two transducers 32 at the heel area. The configuration for both the left and right foot are symmetrical. All of the transducers outputs are directed via cables 33 and 34 which are then applied to suitable amplifiers for the purpose of developing amplified transducer signals for coupling an analog-to-digital converter and for further processing of the signals.

In any event, the information provided by the transducers associated with the insoles for the left and right feet is extremely important and useful information.

As one can ascertain from FIG. 2, there are virtually many types of configurations which can accommodate the types of transducers located in each of the insoles. It is further understood that the insoles can be separate sandals or used in conjunction with other devices as inserts such as sneakers, walking shoes and so on. The main aspect is to generate signals proportional to the pressure applied on the various areas of the foot while the subject being monitored is walking or running.

Referring to FIG. 3, there is shown a typical transducer as employed in conjunction with the insoles of FIG. 2. Essentially, the transducer is a variable resistance device which consists of a first top layer 41 of copper and a second bottom layer 42 of copper. Layers 41 and 42 function as contact areas. Disposed between the copper layers 41 and 42 is a anti-static foam which is a carbon fiber pad. The carbon fiber pad is a variable resistance device and will exhibit a resistance output according to the pressure applied. The entire unit is extremely small and may for example be a ¼ inch in diameter. Essentially, coupled between the electrodes 41 and 42 is a variable resistance device 44 which may be a potentiometer utilized to adjust the quiescent resistance value. The potentiometer 44 may be remotely located as on the amplifier board.

The contacts or layers 41 and 42 are directed to suitable outputs terminals, and as shown in FIG. 3. One terminal is coupled via resistor 45 to a point of operating potential while the other terminal 42 is coupled to ground. As one can ascertain, the output designated as V IN is a function of the resistance or pressure which is exerted between terminals 41 and 42 and which resistance varies as a function of the pressure applied to the carbon fiber pad 43.

Thus, as one can ascertain, there are essentially 14 outputs developed by the left and right insoles in regard to the fact that each insole has seven transducers associated therewith. These outputs are directed via the cables 33 and 34 and are directed to the input of operational amplifier circuits which are shown in FIG. 4.

Referring to FIG. 4, there is shown the operational amplifier configurations which are utilized in conjunction with the pressure transducers as for example shown in FIGS. 2 and 3. Each transducer is associated with a separate operational amplifier configuration. For example, the output of transducer 29 would be coupled to input terminal 50 of the first operational amplifier designated by numeral 46. It is seen that this operational amplifier is a conventional configuration. The output of operational amplifier 46 is coupled to a second operational amplifier 47 which provides an amplified signal at the output designated as A/D for the first channel designated a C-0.

As indicated above, since there are 14 channels, there are 14 operational amplifier configurations as indicated by the dashed lines. Each operational amplifier is an identical circuit configuration as shown for example in regard to operational amplifier 46s and 47. As indicated above, there are also positioned on the subject 10 EMG transducers as 25. These transducers operate to monitor muscle activity, and many examples of such transducers are available in the prior art.

In any event, these transducers may be piezoresistive devices which monitor muscle contraction and provide forces or outputs as a function of such contractions. As one can ascertain from FIG. 4, the EMG transducers occupy two additional channels—namely, channels 14 and 15 and also include a high gain operational amplifier 60 at an input. The operational amplifier 60 is arranged in a differential configuration due to the fact that EMG transducers contain balanced outputs which are applied to terminals 61 and 62. The output of the differential amplifier configuration 60 is applied to a second amplifier 62 arranged in an inverting configuration whose output is applied to a third operational amplifier 63.

The output from the EMG channel is coupled via capacitor 64 to the A/D converter. As one can see, the output of amplifier 63 is designated as C-14 indicating the fourteenth channel in the system. There is an additional channel for an additional EMG transducer which is shown as output amplifier 65 whose output is coupled via capacitor 66 to provide an output signal to the A/D converter which is designated as C-15. Thus, as one can ascertain, there are 14 channels associated with the insoles 27 and 28 of FIG. 2. Fourteen channels accommodate the pressure transducers located on each of the insole devices while two channels accommodate the EMG transducers such as transducer 25 and are operative to provide additional information. It is again clearly understood that there is one complete amplifier configuration as for example amplifiers 46 and 47 for the pressure transducers as 29-32 associated with the insoles 27 and 28. There are two additional channels for the EMG transducers which essentially are identical and include the amplifier configurations as for example 60, 62 and 63.

Hence, as one can ascertain, the system which is associated with measuring force or pressure on each foot of the subject 10 consists of 16 channels where 14 channels are confined to monitoring pressures at the locations indicated in FIG. 2 while two channels are reserved for measuring muscle forces and are a function of where the EMG transducer as 25 is positioned on the subject.

It is of course understood that the insoles for example as shown in FIG. 2 are supplied in various sizes to accommodate different foot sizes. For present purposes it has been determined that six pairs will be employed in order to accommodate the various foot sizes as for example for females, males and children. It is also understood that the amplifier configuration as shown in FIG. 4 consist of conventional commercially available integrated circuit amplifiers which are manufactured by many sources. Hence, the amplifiers 46 and 47 consist of integrated circuit operational amplifiers sold by many manufacturers under the designation as 324. The amplifier such as 60 is sold by a company called Analog Devices under the nomenclature 521 while amplifiers 62 and 63 are high-gain operational amplifiers sold under the designation 741 and manufactured for example by Fairchild Semiconductor of California.

Figure 5:
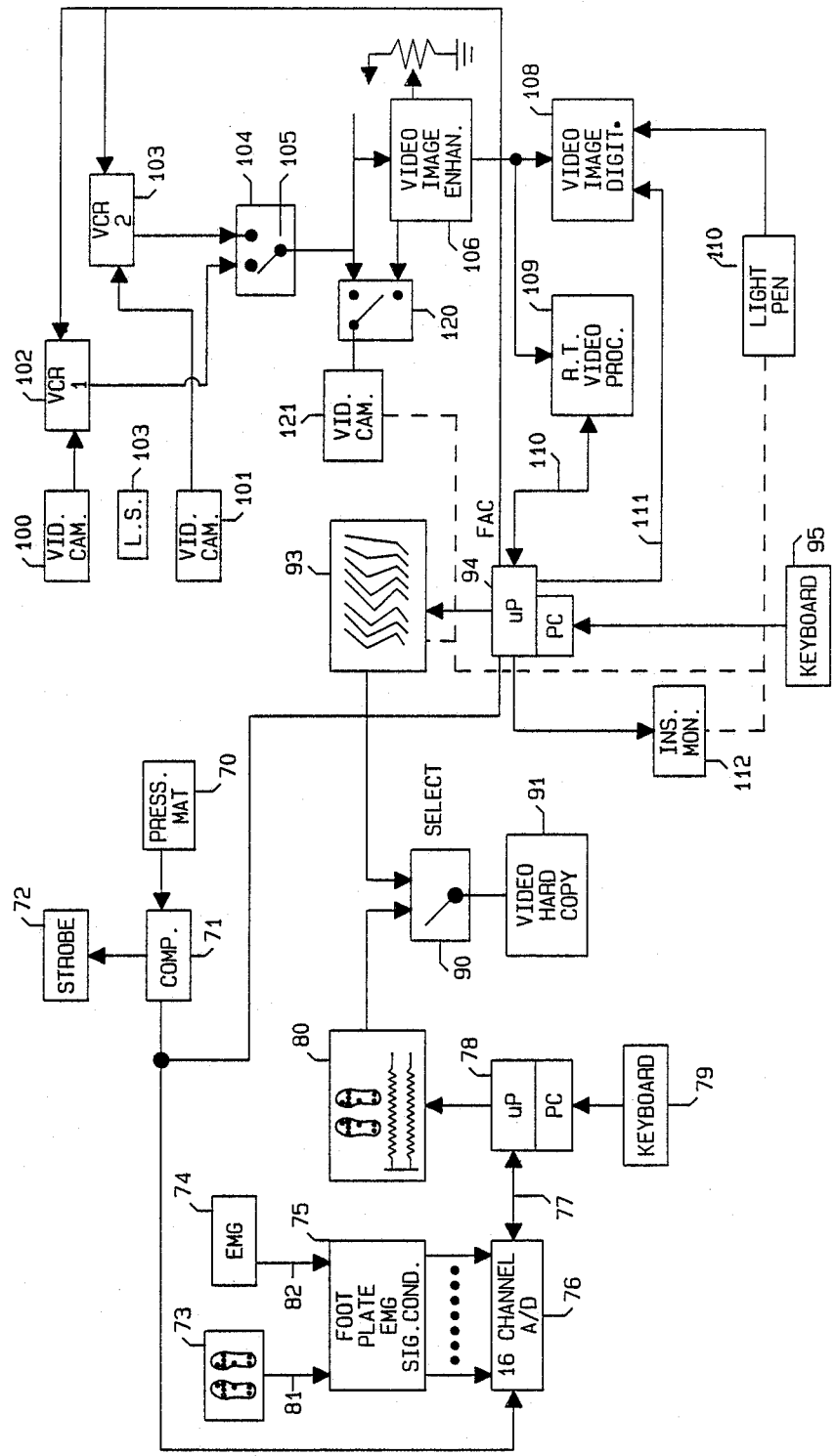
FIG. 5 is a detailed block diagram of a motion analysis system according to this invention.

Referring to FIG. 5, there is shown a detailed block diagram of the motion analysis system. As seen from the left-hand section of FIG. 5, there is shown a module 73 which essentially includes the two pressure sensitive foot insole devices as worn by the subject and for example as shown in FIG. 2. These devices are coupled via cables 81 to the foot plate and EMG signal conditioner circuit 75. Circuit 75 includes the various amplifiers as for example explained in conjunction with FIG. 4. Thus, in a similar manner the EMG sensors 74 are coupled via cable 82 to the foot plate and EMG signal conditioner module 75.

The output from the signal conditioner module 75 which essentially is the output from the 16 amplifiers are applied in parallel to the inputs of a 16 channel A/D converter 76. The output of the A/D converter 76 is coupled via a bidirectional bus 77 to a PC or microprocessor 78. For example, the microprocessor 78 can be a conventional IBM PC unit which typically is associated with a keyboard 79 and a display 80.

As shown in FIG. 5, the pressure mat is designated by reference numeral 70 and is coupled to a comparator 71 whose output is coupled to a strobe 72. The video output of the display 80 is coupled to one input of a switch 90 having a common terminal coupled to a video hard copy or printer device 91. Essentially, the printer device 91 can provide a hard copy of the exact data displayed on the display 80. Such printer devices are conventional devices and are available from many commercial entities.

As will be further explained the switch 90 has a second input terminal which is coupled to a second display 93. The display 93 is associated with a second PC or microprocessor 94 which is also associated with its own keyboard 95. The microprocessor 94 as will be further explained is used in conjunction with the two video cameras as for example those cameras shown in FIG. 1 to provide a front and a side view. The video cameras are designated in FIG. 5 as camera 100 and 101. Each camera is associated with a video tape recorder or VCR device as 102 which is coupled to the output of camera 100 and 103 which is coupled to the output of camera 101. The cameras may be associated with a separate light source 133 depending on the ambient conditions of the room. The video output from each of the VCR's is coupled to a selector switch 104 whereby the movable arm 105 of the selector switch can couple the video output signal from each video recorder respectively to a video image enhancing circuit 106. The video enhancing circuit as will be explained operates to provide stable synchronizing signals to the video digitizer unit 108 and the real time video processor 109.

As seen, the outputs from the video image digitizer 108 and the real time video processor 109 are coupled to the computer or microprocessor 94 via bidirectional cables 110 and 111. The video image digitizer 108 is associated with a light pen device 109 which also may operate in conjunction with the display 93. Also seen in FIG. 5 that is the output of the video image enhancer 106 is coupled to one input of a switch 120 while the other input of the switch 120 receives an output signal from either of the selected video tape recorders. Coupled to the switching terminal of the switch 120 is a video monitor 121 which will therefore operate to provide a display of the image from either video recorder 102 or 103 as selected or provide a video display directly from the video image enhancer circuit 106.

As one can ascertain from FIG. 5, there is shown in block diagram from a complete motion analysis system which motion analysis system may provide a plurality of data indicative of gait as well as .the foot pressure of a subject being monitored by the system. A brief description of the operation will be explained in conjunction with the apparatus briefly outlined above for FIG. 5. As one will recall from viewing FIG. 1, the subject 10 to be tested is fitted with plurality of reflecting markers or light emitting markers such as 13, 15 and so on. The subject also has EMG sensors as 25 positioned at desired body joints. As also described in FIG. the subject also wears the pressure sensitive insole or pressure shoe devices as 27 and 28 of FIG. 2. Essentially, the subject is then directed to step upon the pressure mat 70 during the walk. As he is walking he is monitored by the video cameras as 21 and 22 (FIG. 1) which are analogous to cameras 100 and 101 (FIG. 5). Such cameras are C.C.D. devices available from many sources. Essentially, when the subject steps upon the pressure mat 70 the pressure cause a switch closure. The comparator 71 is a simple electronic circuit having a variable resistance in order to set a variable threshold.

This threshold specifies the minimum weight which is necessary to activate the circuit and activate the strobe. As seen, the output of the comparator energizes the strobe 72 which thereby produces a flash of light. It is noted that the light flash lasts for approximately 1/2 a frame duration and hence the timing of the same is not critical.

In any event, as indicated above, the generation of the strobe enables one to determine the frame processing sequence as will be explained. As one can see from FIG. 5, upon generation of the strobe the 16 channel A/D converter 76 is activated and operates to multiplex and convert 16 inputs into digital signals. These are transmitted to the microprocessor or the PC 78. Based on conventional programs in memory, the PC stores the digital data in assigned memory locations and then processes the data according to predetermined algorithms.

As seen in regard to FIG. 5, the display 80 contains a pictorial representation of the two insoles as for example those shown in FIG. 2 as 27 and 28. This graphic representation of the insoles is displayed directly on the display screen 80. The generation of patterns is well known in the prior art and many such patterns are provided by computer assisted design (CAD) and other techniques. In any event, the microprocessor converts stored digital signals indicative of each transducer associated with each insole into pressure outputs and hence the display 80 as will be seen provides a display of foot pressure versus time. The pressure is the pressure exerted on the subject's foot by each of the pressure transducers.

The display will also present a real time output of the EMG transducer output vs. time as will be further described. This therefore enables the practitioner to determine the exact pressures applied on the feet of the subject during a walking procedure to determine whether excessive pressures are being generated by the user and hence to correlate such pressures or forces with the problem associated with the user's walk or gait.

Figure 6:
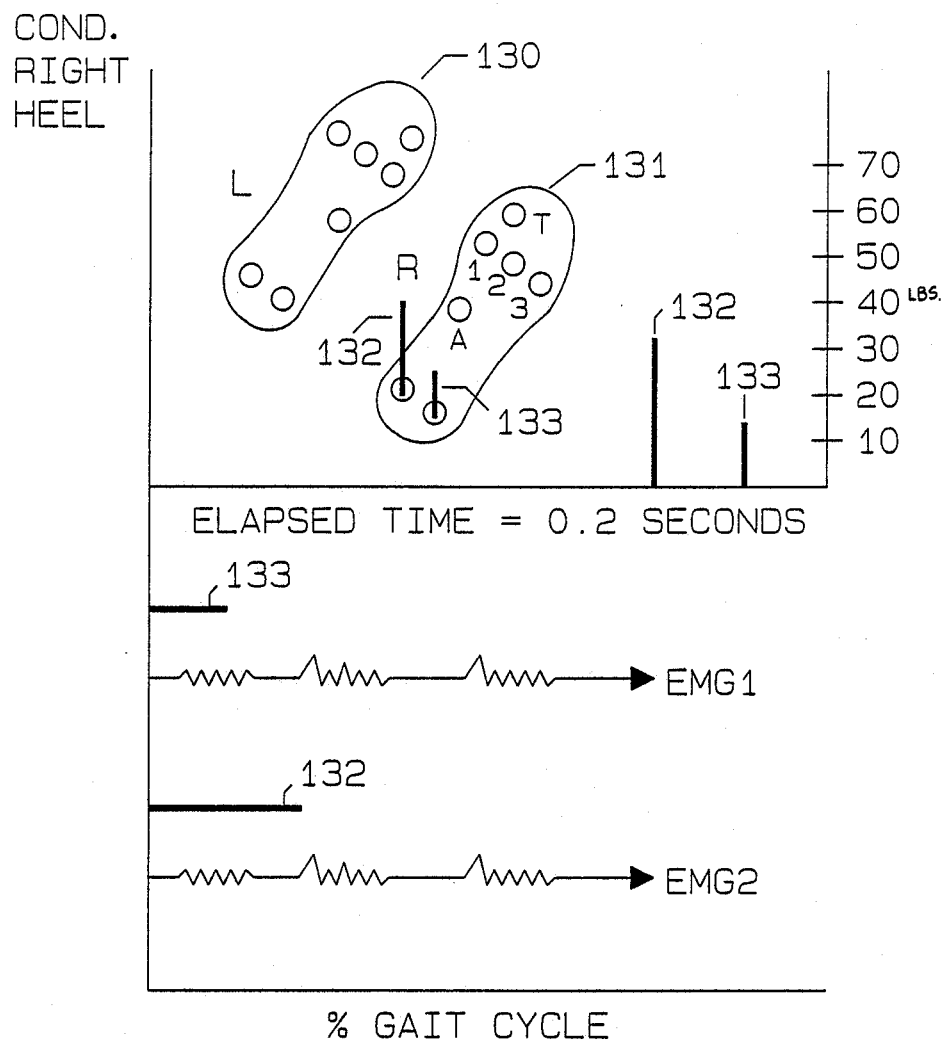
FIG. 6 is a diagram of a typical display generated according to this invention.

Referring to FIG. 6, there is shown a typical display which would appear on the display 80 associated with the PC 78. As one can see from FIG. 6, numerals 130 and 131 represent a computer generation or a computer picture indicating the relationship and the nature of the foot pads or foot insoles as 27 and 28 of FIG. 2. One can also visualize from the display that each position transducer is indicated. The Y axis of the display indicates the term "condition right heel". The user via the keyboard can select any one of a number of displays associated with the insoles 130 and 131. Hence, he can request a display of the right heel, a display of the right arch, a display of the left heel, a display of the left arch or a display of all pressure at all areas.

As seen in FIG. 6, there is displayed the condition of the right heel vs. time. In fact, there is displayed a condition of the right heel vs. an elapsed time period of 0.2 seconds. As seen in FIG. 6, at the heel locations, there is a large bar emanating from the location of one heel transducer designated by 132 and a smaller vertical bar emanating from the heel location designated as 133. As seen to the right are the bars 132 and 133 which are compared along a pressure scale whereby the magnitude or height of the bars is a function of the pounds exerted at each point. In this case for example bar 132 corresponds to a pressure or force of about 35 pounds while 133 approximately corresponds to 20 pounds. Hence, the user has a visual presentation of the pressures applied to the heel area of the right foot and the indication of the magnitude the force or pressure.

Located below and also displayed are the outputs of the EMG sensors such as sensor 25 associated with the subject. The outputs are displayed in real time and it is noted that there are again bars designated as 133 and 132 which are associated with the EMG outputs to enable the practitioner to determine what the EMG status of the muscle transducers positioned on the subject were during the displayed condition of the right heel.

It is understood that programs to covert digital signals to pressure or force and to provide such displays as shown in FIG. 6 are well known in the art. It is further understood that such diagrams enable a practitioner to determine many aspects of a patient's problems and further enables the practitioner to immediately determine in real time what forces are exerted by the patient during the walking procedure. This is evident in regard to FIG. 6. It is again understood that this is one particular type of display which can be implemented according to the outputs of the 14 transducers associated with the foot insoles as well as those transducers which are associated with other characteristics of the patient.

Thus, as one can ascertain, the entire display as well as data processing associated with the pressure sensitive foot insoles is a very important aspect of this invention and can be used in conjunction with or separately from gait measurement apparatus to be described. The practitioner can utilize the switch 90 to select or provide a hard copy printout of the display on monitor 80 during any desired condition. The printout would appear exactly as in FIG. 6 if this were selected. As indicated in FIG. 1, the apparatus also provides a real time motion analysis of the user's walk or gait as implemented by the markers positioned on the user and as shown for example in detail of FIG. 1. Thus the video cameras 100 and 101 are focussed upon the patient and the contents or video output signals of the cameras 100 and 101 are respectively applied to the inputs of the video tape recorders 102 and 103. Hence, the entire walk of the subject is stored on the tape associated with the recorders 102 and 103. Again, via switch 104 the practitioner can select either tape recorder 102 or 103 and couple that tape recorder for example via 120 to video monitor 121. Hence the user has the option to apply the output of either tape reorder 102 or 103 to the video monitor 121 via the switch 120. The output from switch 104 via the contact 105 is also applied to a video image enhancing device 106 associated with a potentiometer. As will be explained, there is a major problem in regard to all motion analysis systems. The problem is as follows. In order to process the signal emanating from a video tape as for example employed with tape recorders 102 and 103, one must employ both horizontal and vertical sync in order to provide address information for the generation o various pixels. This address information is derived from horizontal and vertical scanning pulses in order to enable one to determine a field or a portion of a field as well as a television line.

In this way pixels are generated by conventional television line counters as well as a frame counter to determine that the correct number of pixels for each frame is in fact implemented. In regard to the above, one of course understands that horizontal and vertical sync are utilized. In any event, as one will also understand, it is a severe problem to maintain accurate indications of horizontal and vertical sync as supplied by the video tape recorders due to inherent errors produced in the video tape recording process.

These errors reside in jitter, tape stretching and so on whereby the sync pulse is not stable enough to generate a proper reference for the digital processing equipment. As will be explained, the video image enhancer essentially consists of a separate television monitor which provides a television picture of the video tape signal which is being supplied to the video image enhancer. The screen of this television monitor is then monitored by a separate video camera having a wide angle lens and a configuration as cameras 100 and 101. This camera actually produces a video output signal according to the display on the video monitor and this signal is employed by the video digitizer to produce a pixel array of each particular frame.

Thus, as shown in FIG. 5, the output of the video image enhancer 106 is coupled to a video image digitizer 108 and a real time video processor 109. Both the real time video processor 109 and the video image digitizer 108 are coupled to the PC via bidirectional cables 110 and 111. As one can immediately understand, the function of the video image digitizer is to digitize each frame to produce a number of pixels corresponding to each frame. These pixels are utilized to determine the position of the markers associated with the subject and hence to provide a display be indicative of the markers and presented in an understandable format. If one refers to certain of the prior art articles, such displays are referred to as stick-figure displays whereby the position of the markers for example as those shown on the subject of FIG. 1 will produce a stick figure of the entire leg of the subject starting from a marker at the hip, a marker at the knee, a marker at the ankle and a marker at the toe.

These four markers when connected by suitable lines will produce a stick figure representation of the subject's leg showing each and every angle associated with the various leg joints such as the angle of the hip, the angle of the knee and so on. Such displays are well known and for example have been described in conjunction with the above noted patent, U.S. Pat. No. 4,631,676.

Techniques for generating such displays are also known. In any event, such displays provide useful information necessary for proper analysis of the gait of a patient. The real time video processor 109 is also employed in the event that the practitioner wishes to see the exact subject in a true video presentation. In any event, real time data is also processed via the microprocessor or PC 94 via the real time processor.

There is also a keyboard 95 associated with the PC which keyboard 95 enables the operator to implement various displays as well as various routines according to the selected keyboard instruction. The instruction monitor 112 is coupled to the microprocessor 94 and will enable the user to visualize, if desired, various functions performed by the microprocessor. Also associated with the PC or microprocessor 94 is the display 93. As seen, the display is showing a depiction of the leg movement of the subject over a period of time and represented by stick-figure outputs.

There is a light pen 109 which is associated with the video image digitizer and which enables the practitioner to select the markers by means of the light pen and to therefore indicate the exact markers associated with each frame. As indicated, each VCR as 102 and 103 is associated with a frame freeze operation whereby each and every frame recorded on the VCR can be frozen in time. Such VCR's employing such techniques are well known in the art and for example are implemented by a VCR sold by Sony of Japan under the designation SLMF-900. There are many other VCR's available which will provide a frame freezing operation.

In any event, as indicated, the practitioner first will locate the first frame after the strobe frame. The strobe frame is easily visualized by the practitioner by reviewing the tape and determining the bright light flash. Thus, the selected frame is frozen by means of the video tape recorders and the video signal is passed through the video enhancer circuit: where the brightness of the video monitor can be controlled to enable the user only to see dot representations or spot representations of the markers. Typically, the markers will be brighter than the rest of the area being televised, and hence the user by adjusting the brightness of the video monitor contained in the video image enhancer 106 can present a picture whereby only the markers will be highlighted.

The user then takes the light pen and manually selects the location of each marker. Once this is done the system via the microprocessor 94 will perform an edge detection algorithm program whereby the outline of the selected markers will be traced and the center of each marker will be calculated. As will be further explained the technique employs an eight position edge detection scheme. In any event, the operator or user initially locates each marker in each frame by means of the light pen. He does this by visually looking at the display and placing the light pen at the location of each marker.

As above indicated, it is possible that during the walking procedures and based on rotation of the subject's body, arm swing and so on, various markers may be missing. In any event, the user or practitioner knows which markers are missing by viewing the entire frame, and hence he can approximate or place the missing marker in a proper position thereby filling in the data.

Thus, if a marker is missing, the operator uses the cursor or light pen to locate the proper joint position and does this manually. After all the markers are located either by the edge detection technique to be described or by the manual technique, the frame is then advanced to the next frame and the above procedures are repeated. As one can see, an output of the microprocessor 94 is designated as FAC which is a frame advance control. This frame advance control is generated by the microprocessor and sent to VCRs 102 and 103 to advance the VCRs to the next frame.

All data indicative of the joint positions of the subject is digitized by means of the digitizer 108 which produces a pixel presentation or array for each frame.

Figure 7:
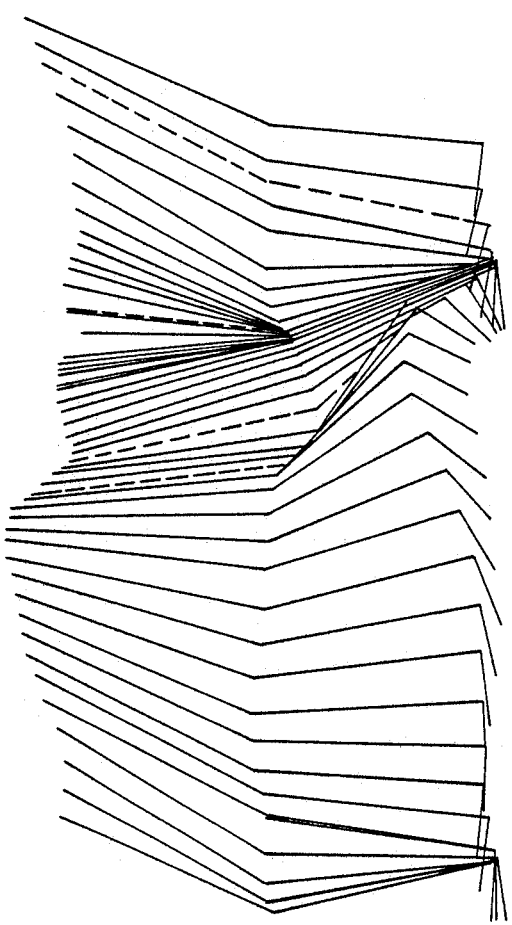
FIG. 7 is a diagram of another type of display generated by the apparatus.

Referring to FIG. 7, there is shown a typical stick-figure presentation corresponding to the leg motion of a subject during a particular interval. Also seen in FIG. 7 is various data which may be included and other calculated date. Programs for doing this are known in the art, and see for example the above-noted patent. After all of the coordinates have been processed by the computer for each frame of the video record, the body segments and joints of interest are known. The data collected is processed by the microcomputer for analysis and the microcomputer typically provides calculations and the data presentation. The various programs for producing stick figures of any degree of complexity upon operator request are also well known. Essentially, one determines the exact position including the exact coordinates of each marker indicative of the hip, knee, ankle and toe and utilizes these coordinates for providing computer processing.

Thus, the display as shown for example in FIG. 7 is a typical display which will be provided and which is available from the data generated by this system.

Figure 8:
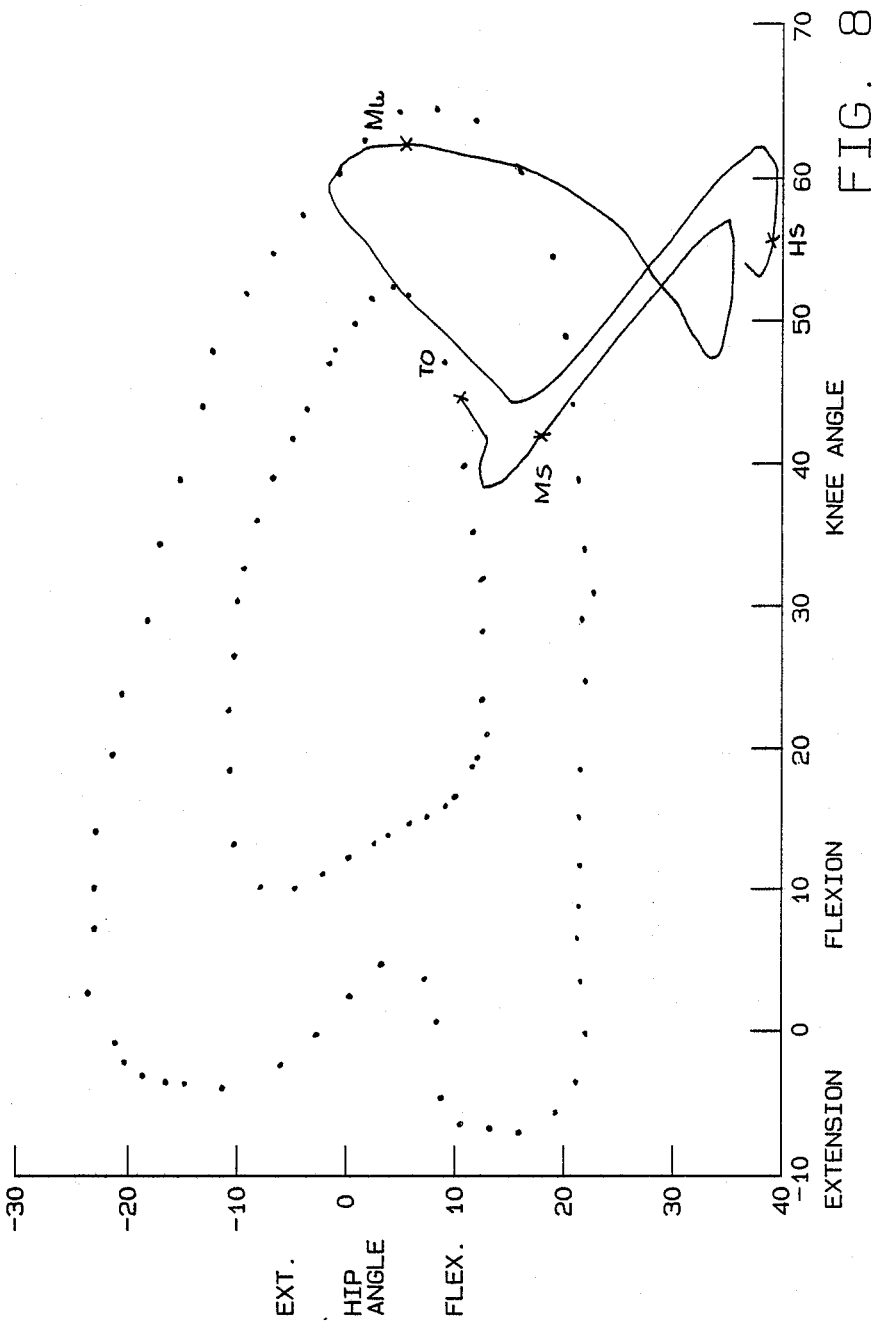
FIG. 8 is a diagram of still another type of display generated by the apparatus.

Referring to FIG. 8, there is shown another type of display which can be provided. The display shown in FIG. 8 is referred to as a cyclogram and such cyclograms are also obtained from the data. Such a cyclogram depicts the angular relationship of two joints during a cycle of motion, and for example the cyclogram in FIG. 8 shows the hip angle both in extension and flexion as compared for example to the knee angle.

The degree of smoothness and openness of the cyclogram is used in the art to be a good indicator of the relative normalcy of the motion afforded by the subject. In this manner, certain orthopedic conditions can be quantized quite readily through the depiction of these plots and such plots can be compared with normal plots for normal individuals.

Shown in FIG. 9 are two additional displays which can be formulated and displayed. The top figure in FIG. 9 shows the hip angle vs. the percent of the gait cycle wherein the dashed line shows that same exact hip angle vs. percentage of gait cycle for a normal user. The bottom display of FIG. 9 shows the knee angle vs. the percentage of gait cycle while the dashed line again shows that for a normal user. Hence, the amount and number of displays provided by the motion analysis system as above described are substantial.

Thus, the data, stick figures, and cyclograms which are generated by this system provides an orthopedic surgeon, neurologist and other physicians interested in gait with effective tools used in diagnosis and treatment. As one can understand, the system allows not only the gait to be broken down into various displays but also uniquely provides force or pressure outputs implemented with the foot pads worn during the generation of the above-noted gait data. This is extremely useful in providing diagnosis of all particular sorts for different physical handicapped users.

Figure 10:
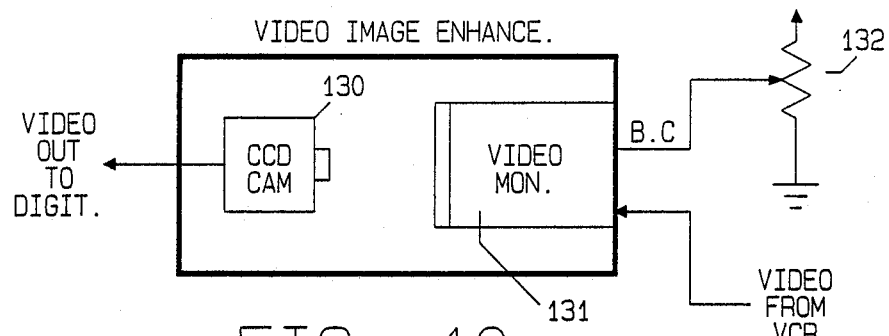
FIG. 10 is a simple block diagram showing a video image enhancer according to this invention.

Referring to FIG. 10, there is shown a schematic diagram of the video image enhancing unit for example that unit 106 depicted in FIG. 5. As explained, the video image enhancing unit contains a video monitor 131 which displays a picture according to the video input from the video tape recorder or VCR device. A potentiometer 132 is coupled to the brightness control of the video monitor to enable the practitioner to vary the brightness of the picture displayed on the video monitor until a proper picture is displayed. This picture may show only the markers. The video monitor is scanned by means of a C.C.D. camera or video camera 130 which provides a video output signal which is directed to the digitizer as well as to the real time video processor as for example modules 108 and 109 of FIG. 5. In this manner, the video camera 130 produces an extremely stable sync which is indicative of sync fluctuations which may emanate from VCR 100 and 101. In this manner, the video signal which emanates from camera 130 and is utilized by the video image digitizer 108 and the real time video processor 109 is extremely stable.

Figure 11:
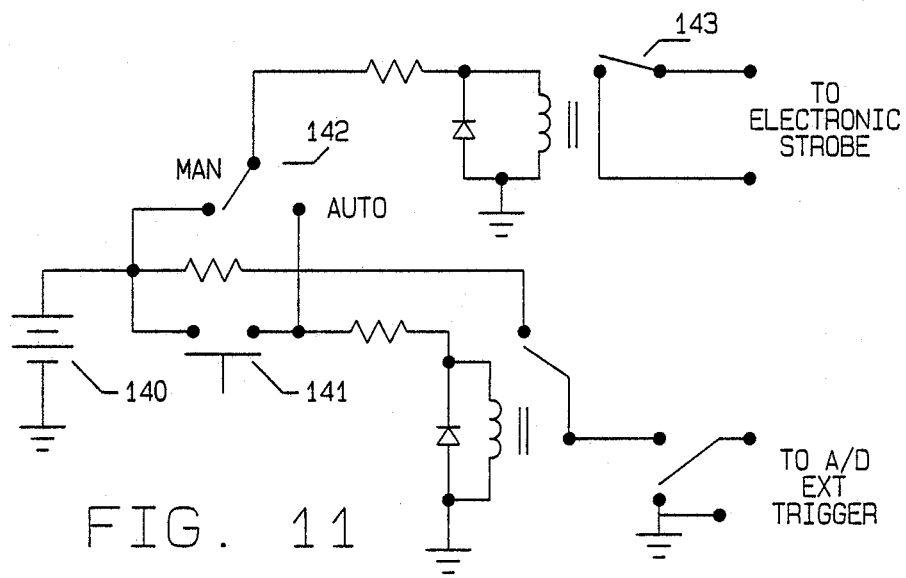
FIG. 11 is a schematic circuit diagram of a switching apparatus used in conjunction with a pressure mat according to this invention.

Referring to FIG. 11, there is shown a simple block diagram of the circuitry associated with the pressure mat as for example the mat 70 of FIG. 5. It is noted that the circuitry is included in the comparator circuitry 71. Essentially, the circuitry contains a manual, and automatic switch 142. When the switch 142 is placed in the manual position, the relay 143 is automatically closed as can be ascertained. The closure of relay 143 provides a short circuit input to the electronic strobe which therefor generates the strobe pulse. The closure of the switch 142 also activates relay 144 which sends a positive signal to the A/D converter for example that converter designated as 76 of FIG. 5. If the switch 142 is placed in the automatic mode, it is seen that the pressure mat 141 generates a closure. The closure of the pressure mat switch 141 causes the above-noted sequences to be implemented—namely, the operation of both relays 143 and 144 to thereby activate the strobe and to provide the start signal to the A/D converter. It is of course understood that there are many techniques for implementing such circuitry.

In any event, the use of the relay is very cost effective and will operate to activate both devices at the proper time. It is of course understood that the general operation is that upon closing of the mat switch 141, the switching circuit must be able to activate the A/D converter and generate the strobe. The A/D converter is typically activated by a 5 volt positive edge pulse to its input terminals.

The strobe device is activated by short circuiting its input terminals. The relays as 143 and 144 provide cost effective means to activate these devices as indicated above. Thus, as one can ascertain, the user has the ability to manually or automatically activate the system as desired. The diodes which are positioned across the inputs of relays 143 and 144 will prevent back EMF from tripping the circuit a second time and further serves to protect the relays.

Figure 12:
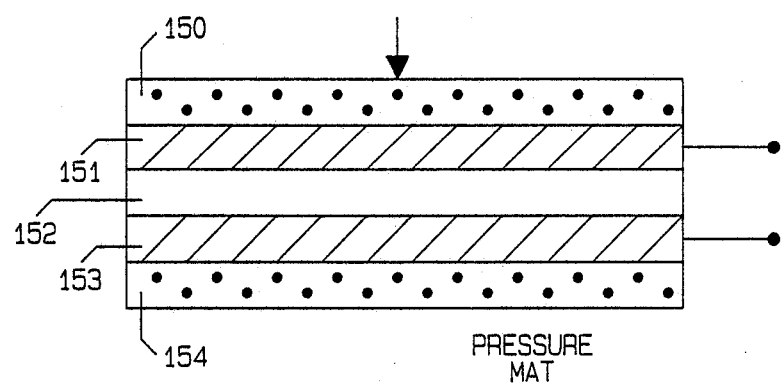
FIG. 12 is a simple cross sectional view of a pressure mat according to this invention.

Referring to FIG. 12, there is shown a simple cross sectional diagram of a pressure mat which can be employed for pressure mat 11 or pressure mat 70 of FIG. 5. Such devices are well known in the prior art and are available from many commercial manufacturers.

Pressure mats are available from many sources as indicated above. The typical pressure mat employs a first layer of plastic or other insulating material 150 which covers a conductive foil layer 151. Foil layer 151 may be made of copper or a suitable conducting metal. The foil layer 151 is separated by an air space 152 from another conductive foil layer 153 which also has on its bottom surface a layer of insulating material 154. As one can ascertain, when a pressure is applied in the direction of the arrow, layer 151 contacts layer 152 providing a short circuit at the output which essentially is a of an extremely small impedance which is less than 1/10 of an ohm.

Figure 13:
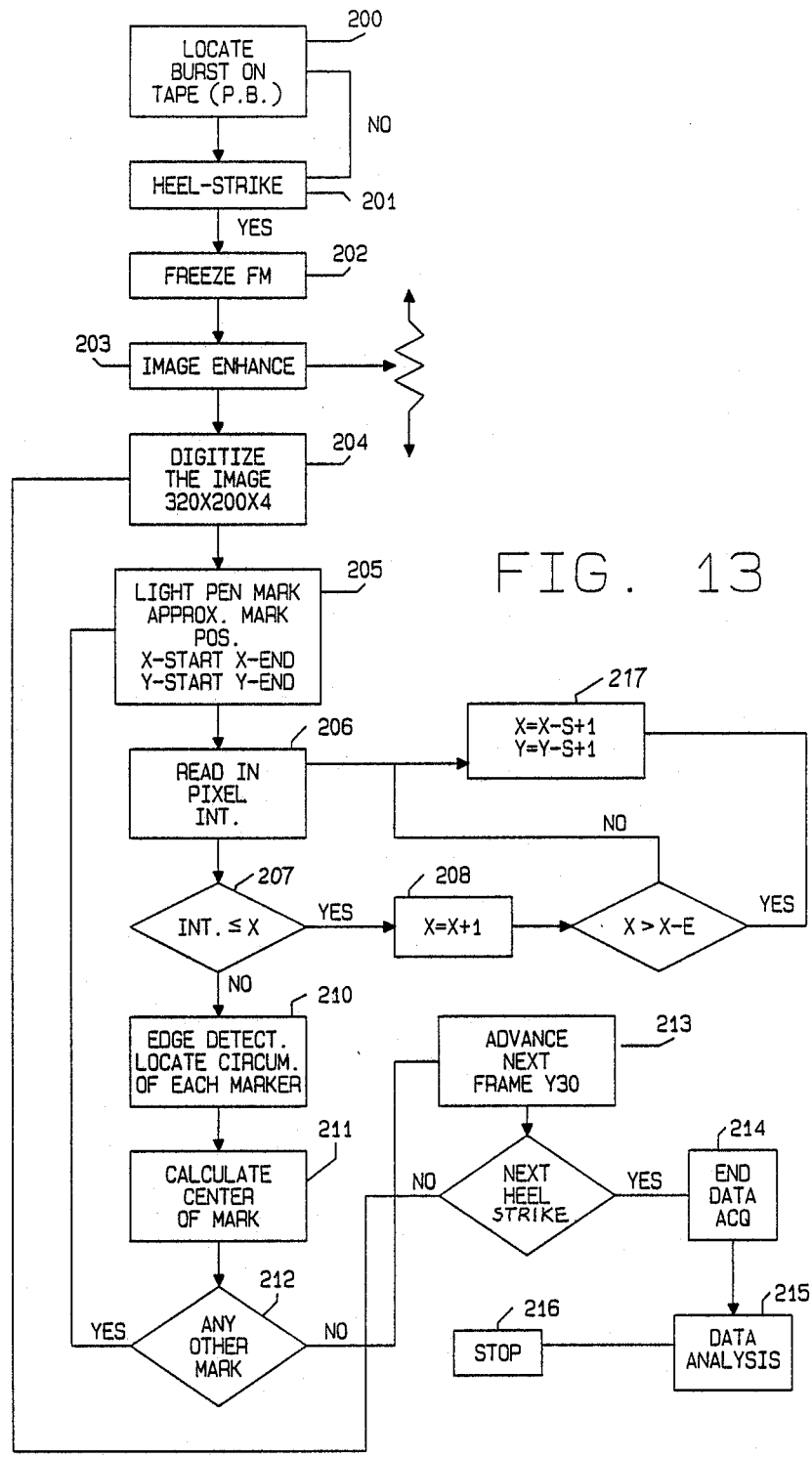
FIG. 13 is a flow chart depiction of the operation of the apparatus of FIG. 5.

Referring to FIG. 13, there is shown a flow chart of the motion analysis system above described. It is indicated that the flow chart depicted should be sufficient for one skilled in the art to understand the operation of the above-described structure as for example that depicted in conjunction with FIG. 5.

It is further indicated that the entire program which consists of over 200 pages is the subject matter of a copyright which has been applied for by the assignee herein and which copyright is entitled REAL TIME MOTION ANALYSIS SYSTEM and owned by Human Performance Technology, Inc., the assignee herein. That copyright has been applied for prior to the filing date of this application and contains all software and program information necessary to implement the entire system and according to the general description as shown in FIG. 13.

Referring to FIG. 13, there is shown a first block designated as 200. Essentially, as described in detail above, the practitioner locates the strobe burst on the tape during playback. This is indicated by module 200. It is of course understood that this location corresponds to the burst of light generated by the strobe when the subject accesses the pressure mat or during the manual mode. In any event, he then determines whether or not there is a heel strike. If it is not a heel strike, the burst is again located so that he can make sure that at least one heel of the subject touched the mat and uses this as a first frame.

If it is a heel strike as indicated in module 201, the frame is then frozen as indicated by module 202. As indicated above, the tape recorders utilized employ a framefreeze process which is a well known technique associated with most tape recorders. Once the frame of interest is frozen as indicated by module 202, the image enhancer is then adjusted by means of the potentiometer as indicated by module 203 until the desired image is displayed. As indicated, one has the ability to control the brightness of the monitor so that the video display only shows the locations of the markers or the user may control the brightness according to any preference he desires. As soon as the proper brightness is selected via the image enhancer 203, the image is then digitized or pixels are generated as indicated in modules 204.

Digitizing of analog video frames is a well known technique implemented by many devices in the prior art. As indicated above, a plurality of pixels are formed for each line in the particular television frame. In this manner, each frame information is stored in the computer by means of digitizing the information as indicated in module 204. The digitized information is also processed according to module 205 by means of the light pen marking scheme whereby the user can in a manual mode determine the proper position of each marker which essentially defines a start and end designated by X and Y for each frame.

The system then reads in the intensity of each pixel associated with each of the markers or other information contained in the image as indicated by module 206. Essentially, a search mode is then implemented as indicated by module 207 whereby the intensity of the desired markers are compared with a predetermined intensity X for example. If the intensity of a marker is less than X then another marker is searched as indicated by 201. Another marker is then determined in regard to intensity. If there is no other marker then the program is told to stop.

If there are other markers then the unit 207 determines when the entire picture has been scanned. If there are no markers remaining whose intensity exceeds the given value of X then all markers have been accounted for and an edge detection search is made which is a routine which locates the circumference of each of the markers as indicated by module 210. Once the location of each marker is determined then the center of the marker is calculated by a suitable program designated by module 211. The unit then looks to see if there are any other markers which may be available in the system indicated by module 212. If there are other markers then the light pen is utilized to fill in for example these other markers or to account for missing markers. If there are no other markers then one automatically advances to the next frame as indicated by module 213. As seen, a frame is 1/30 of a second. During the next frame, one again looks for a heel strike. If there is a heel strike then this ends the data acquisition for that frame as indicated by module 214.

If there is not a heel strike then one proceeds to digitize the information of the next frame following the above-noted procedures until that frame has been analyzed. At the end of data acquisition, all stored data is then analyzed by means of the program stored in the microcomputer as indicated by the data analysis block 215, and when all data has been properly analyzed, there is a stop which is indicated by the stop module 216. It is of course understood that such programs are capable of being implemented by those skilled in the art as evidenced by some of the above-noted references and further all such programs are contained in the above-noted copyright which is deemed to be part and parcel of this application.

Figure 14:
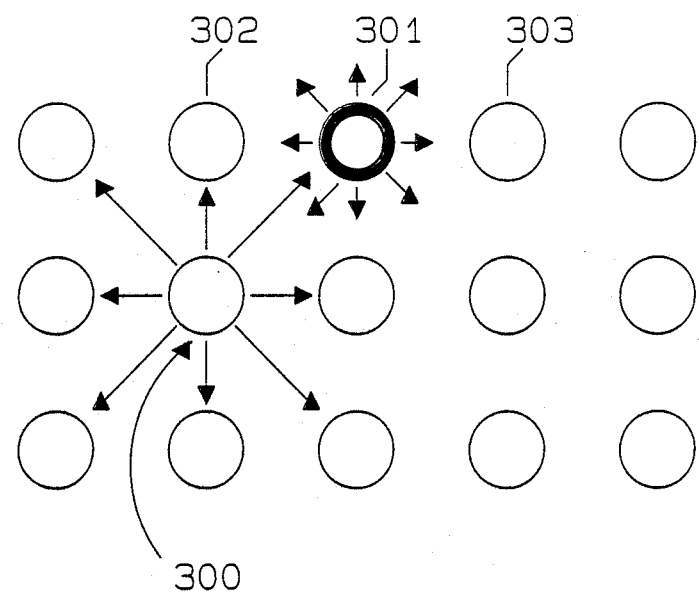
FIG. 14 is a simple diagrammatic view necessary to explain the technique for location of various markers according to the details of this invention.

Referring to FIG. 14, there is shown a simple diagram depicting the edge detection routine which essentially is applicable to determine the marker location according to the techniques described above.

As seen in FIG. 14, a first marker of a given intensity is selected. This is designated as marker 300. The intensity of this marker is compared with the intensity of all eight markers which surround the same. It is of course understood that each marker is in fact definitive of a pixel location and defined in terms of XY coordinates in regard to the video display. Thus, each marker depicted has particular X and Y locations or coordinates in regard to a full video frame. The marker 300 is compared in intensity with all eight markers and for example as shown in FIG. 14, there is a marker 301 which is of greater intensity than marker 300. The marker 301 could also be the marker which is the true marker while the marker 300 may be an undue reflection or ghost. In any event, if the intensity of marker 301 exceeds the intensity of marker 300 then marker 301 is now designated and this marker is again compared with all eight adjacent markers surrounding the same as further indicated in the diagram.

In this manner, the intensity of all markers are compared in surrounding groups until the brightest marker in a given location is located. This is designated to be a true marker. In any event, once this marker is determined one looks at adjacent locations or adjacent pixels as for example 302 and 303 to determine relative intensities. It is again noted that the circumference of the marker will be of a less intensity for example than the center of the marker. This is especially true when one utilizes an LED or a light emitting device whereby the light emitted at the center will be brighter than the light of the edges. In this manner by investigating all neighboring markers, one can therefore accurately locate the exact position and area of the marker desired.

All the coordinates are stored whereby the center of the marker is then computed to enable one to utilize this as one point in the generation of the stick figure presentation of the subject's leg and so on. This technique is also implemented by a very simple programming procedure and avoids some of the complicated algorithms associated with prior art devices. Thus, as one can ascertain from the above, there is described a motion analysis system employing many features which will enable a practitioner such as an orthopedic surgeon or other physician to determine the exact nature of a person's gait as well as pressure applied to the feet of a person during a walking procedure. In this manner, the practitioner has various data and different types of displays to fully analyze the patient's handicap with the above described system.

What is claimed is:

1. A motion analysis system of the type operative to analyze the movements of designated body portions of a subject to be monitored as the subject walks along a predetermined path and to particularly analyze the pressure applied to the feet of said subject when traversing said path, comprising:

pressure responsive means secured to the feet of said subject and operative to provide output pressure signals indicative of the force applied to the subject's feet while traversing said path, first computer means coupled to said pressure responsive means and operative to analyze said pressure signals to provide a display of the pressure applied to said subject's feet during given selected time intervals as said subject traverses said path and pressure operative means associated with said path and operative to provide an output signal when walked on by said subject with said signal coupled to said first computer means to determine a start of processing.

2. The system according to claim 1, wherein said pressure responsive means includes at least one foot pad worn by said user on a foot thereof said pad containing a plurality of pressure transducers with a first located near the big toe of said user, a second at the arch and a third at the heel whereby each transducer provides an output signal associated therewith and indicative of toe, arch and heel pressure respectively as occurring as said subject traverses said path.

3. The system according to claim 2, further including analog to digital converting means coupled to said pressure transducers for providing separate digital signals indicative of the pressure output of each transducer, with said digital signals stored by said first computer means and processed thereby.

4. The system according to claim 1, wherein said first computer means includes display means for generating a visual display of a subject's foot including a display of the areas being monitored according to said pressure signals.

5. The system according to claim 1 further including a triggerable light source coupled to said pressure operative means on said path and operative to provide a burst of light when said pressure operative means is walked on.

6. The system according to claim 6, further including,
at least one television camera monitoring said path and responsive to said burst to provide a first brightness level indicative of said burst for determining a start analysis frame,
storage means coupled to said camera for storing televisions signals as said subject traverses said path,
digitizer means coupled to said storage means for digitizing said stored signals on a frame to frame basis, with a first frame defined by the frame after said burst containing frame,
second computer means responsive to said digitized signals for processing the same to provide a display indicative of the motion of the subject while traversing said path to enable a user to use said second computer display with said first computer display for motion analysis.

7. The system according to claim 6, further including a video monitor coupled to said storage means for providing a display of said stored video signals and means coupled to said video monitor for providing another video signal indicative of said displayed signal for application to said digitizing means.

8. The system according to claim 7, wherein said means coupled to said video monitor includes a television camera operative to monitor said display to provide at an output said another video signal.

9. The system according to claim 6, further including a light pen means coupled to said digitizing means and operative to modify said stored signals prior to digitizing the same.

10. A motion analysis system of the type operative to analyze the motion of designated body portions of a subject to be monitored as the subject walks along a predetermined path and particularly adapted to analyze the gait, joint angles and force between said body portions and the forces exerted on said body portions as said subject traverses said path with said body portions of said subject marked by light indicating markers, said system of the type employing first and second television cameras and associated storage means as video tape recorders associated with each camera for storing the video signal from each camera and including digital means coupled to said storage means for digitizing said video signals by forming a pixel array and computer means coupled to said digital means for processing said digitized signals to provide displays indicative of the motion qualities of said subject as traversing said path with said displays as provided being processed according to said markers, the improvement therewith of apparatus for controlling the processing of said motion analysis system comprising:
pressure operative means associated with said path and operative to provide a burst of light when said subject contacts said means, with said burst of light responded to by said cameras to provide a first reference video signal which when stored provides a reference video frame for said digital means,
video image enhancing means coupled to said storage means and operative to provide an output video signal from said stored video signal, with said output video signal including stabilized sync components for application to said digital means to enable said digital means to provide stabilized digitized output signals, and
processing means associated with said computer means and operative to determine the location of said markers by comparing adjacent pixels in said array with a given pixel for selecting those pixels of a greater intensity and indicative of a marker's location.

11. The system according to claim 10, further including:
pressure responsive means coupled to the feet of said subject and operative to provide output signals indicative of the pressure applied to the subject's feet when traversing said path, and separate computer means responsive to said burst signal and coupled to said pressure responsive means to process said pressure output signals to provide a display of said signals during selected time intervals as said subject traverses said path.

12. The system according to claim 11, wherein said pressure responsive means includes a right and a left foot pad worn by said subject on each foot, with each pad including a plurality of pressure sensors, with a first sensor located near the toe of said subject, a second near the arch and a third near the heel wherein each sensor on each foot provides an output signal indicating the pressure generated at said location, and
analog to digital conversion means coupled to said sensors and operative to convert said output signals to digital signals for processing said signals to provide said display.

13. The system according to claim 12, wherein said separate computer means is operative to provide a display indicative of the outline of a right and a left foot of a subject and including areas on said display designating said pressure sensor locations, for providing a displayed pressure signal at each location indicative of the pressure at said location during a given time interval as said subject traverses said path.

14. The system according to claim 11, wherein said pressure responsive means includes a pressure mat positioned in said path and operative to provided an output signal when a force is applied thereto indicative of said subject walking on said mat,
a strobe light coupled to said mat and operative to emit a light burst during the presence of said output signal, and control means coupled to said mat and operative to provide a control signal for application to said second computer means.

15. The system according to claim 10, further including light pen means coupled to said processing means and operative to manually mark the location of said markers according to said displayed video signals.

16. The system according to claim 11, wherein said video enhancing means includes a video monitor coupled to said storage means and operative to provide a video display of said stored video signal, a television camera positioned to monitor said display to provide said output video signal for application to said digital means.

17. The system according to claim 16, further including brightness control means coupled to said video monitoring means for adjusting the brightness of said display to enable control of the intensity of said markers as compared to non-marker areas of said display.

18. The system according to claim 16, wherein said television camera is a C.C.D. device.

19. The apparatus according to claim 10, wherein said processing means includes means for comparing the intensity of a given selected pixel with the intensity of surrounding pixels and to select a surrounding pixel of a greater intensity as a correct pixel.

* * * * *